United States Patent [19]
Slabas et al.

[11] Patent Number: 5,843,739
[45] Date of Patent: Dec. 1, 1998

[54] DNA ENCODING 2-ACYLTRANSFERASES

[75] Inventors: Antoni Ryszard Slabas, High Shincliffe; Adrian Paul Brown, Shadforth, both of United Kingdom

[73] Assignee: Nickerson Biocem Limited, Cambridge, United Kingdom

[21] Appl. No.: 454,267

[22] PCT Filed: Dec. 10, 1993

[86] PCT No.: PCT/GB93/02528

§ 371 Date: Aug. 4, 1995

§ 102(e) Date: Aug. 4, 1995

[87] PCT Pub. No.: WO94/13814

PCT Pub. Date: Jun. 23, 1994

[30] Foreign Application Priority Data

Dec. 10, 1992 [GB] United Kingdom .................... 9225845

[51] Int. Cl.$^6$ .............................. C12N 9/10; C12N 15/54
[52] U.S. Cl. .................. 435/172.3; 435/193; 435/252.3; 435/410; 435/320.1; 536/23.2
[58] Field of Search ................................ 435/193, 252.3, 435/252.33, 410, 172.3, 320.1; 536/23.2

[56] References Cited

FOREIGN PATENT DOCUMENTS

| | | |
|---|---|---|
| 0 242 246 | 10/1987 | European Pat. Off. . |
| 0 270 822 A1 | 6/1988 | European Pat. Off. . |
| 0 344 029 | 11/1989 | European Pat. Off. . |
| 0 116 718 A1 | 8/1994 | European Pat. Off. . |
| WO 92/13082 | 8/1992 | WIPO . |

OTHER PUBLICATIONS

Bernerth, R. and M. Frentzen, "Utilization of Erucoyl–CoA by Acyltransferases from Developing Seeds of *Brassica napus*(L.) Involved in Triacylglycerol Biosynthesis," *Plant Sci.* 67:21–28 (1990).

Hares, W. and M. Frentzen, "Substrate specificities of the membrane–bound and partially purified microsomal acyl–CoA: 1–acylglycerol–3–phosphate acyltransferase from etiolated shoots of *Pisum sativum*(L.)," *Planta* 185:124–131 (1991).

Löhden, I. et al., "Acyl–CoA: 1–acylglycerol–3phosphate acyltransferase from developing seeds of *Limnathes douglasii* (B. Br.) and *Brassica napus* (L.)," in: Plant Lipid Biochemistry, Structure and Utilization: Proc. 9th Int. Symp. Plant Lipids, Quinn, P.J. and J.L. Harwood, eds., pp. 175–177 (1990).

International Search Report from Application PCT/GB93/02528 (1994).

Bernerth et al., Utilization of erucoly–CoA by acetyltransferases from developing seeds of *Brassica napus* (L.) involved in triaacylglycerol biosynthesis, *Chemical Abstracts* 113(3):20895a (1990).

Coleman J., Characterization of the *Escherichia coli* gene for 1–acyl–sn–glycerol–3–phosphate acyltransferase (plsC), *Mol. Gen. Genet.* 232:295–303 (Mar. 1992).

Hares et al., Substrate specificities of the membrane–bound and partially purified microsomal acyl–CoA:1–acylglycerol–=3–phosphate acyltransferase from etiolated shoots of *Pisum savatium*(L.), *Chemical Abstracts* 115:201740h (Nov. 1991).

Herrera–Estrella et al., Chimeric genes as dominant selectable markers in plant cells, *EMBO J.* 2(6):987–95 (1983).

Herrera–Estrella et al., Expression of chimaeric genes transferred into plant cells using a Ti–plasmid–derived vector, *Nature* 303:209–213 (1983).

Knauf V.C., The application of genetic engineering to oilseed crops, *TibTech* 5:40–47 (1987).

Loehden et al., Acyl–CoA:1–acylglycerol–3–phosphate acyltransferase from developing seeds of *Limnanthes douglasii* (R.Br.) and *brassica napus* (L.), *Chemical Abstracts* 116(9):79057u (Mar. 1992).

Oo & Huang, Lysophosphatidate Acyltransferase Activities in the Microsomes from Palm Endosperm, Maize Scutellum, and Rapeseed Cotyledon of Maturing seeds, *Plant Physiol* 91:1288–1295 (1989).

Peterek et al., Approaches of cloning the 1–acylglycerol–3–phosphate acyltransferase, 8th Workshop on plant lipid, 90th Conference of the Gesellschaft für Biologische Chemie, *Biol. Chem. 2Hoppe–Seyler* 372(8):539 (Aug. 1991).

Peterek et al., Wege zur Klonierung der 1 Acetylgycerin–3–Phosphat–Acyltransferase, 47th Annual Meeting of the German Society for Fat Science, *Fat Science Technology* 93(11):417–418 (Nov. 1991).

Studier et al., Use of T7 RNA Polymerase to Direct Expression of Cloned Genes, *Methods in Enzymology* 185:60–89 (1990).

Wolter v. et al., Biochemical and Molecular Biological Approaches for Changing the Fatty Acid Composition of Rape Seed Oil, Abstract on p. 288, *Fat Sci. Technol.* 8:288–90 (Jun. 1991).

*Primary Examiner*—Charles L. Patterson, Jr.
*Attorney, Agent, or Firm*—Sterne, Kessler, Goldstein, & Fox PLLC

[57] ABSTRACT

Plants, particularly transgenic plants, may be produced having a 2-acyltransferase enzyme or other insoluble acyltransferase enzyme with an altered substrate specificity compared to the native enzyme. For example, oil seed rape (*Brassica napus*) may contain a 2-acyltransferase transgene derived from *Limnanthes douglassi* in order to increase the erucic acid content of the oil. The cDNA sequence of maize (*Zea mays*) 2-acyltansferase is disclosed and is useful for cloning acyltransferase genes and/or cDNAs from other organisms, including *L. douglassi*.

13 Claims, 8 Drawing Sheets

```
1/1
CCC CGT CCT CCT CGT CGC CGG AGC CGC CGG CGG GAA GGA GCG CCG CGG
 P   R   P   P   R   R   R   S   R   R   R   E   G   A   P   R
                                        31/11
61/21                                   CTA CTA TCG CCT GGA AAG CGG CGC
GGA GCT TTT CCC ACT GCC GAC TGC CGT CTG  L   L   S   P   G   K   R   R
 G   A   F   P   T   A   D   C   R   L
                        91/31
121/41                  ACC CTC CGA GAT CGG CTC GGC CTG CTC TTC CTC
CGG CCG ATG GCG ATC CCG GTC GTG CTC CCG  T   L   R   D   R   L   G   L   L   F   L
 R   P   M   A   I   P   V   V   L   P
                151/51
181/61          GTC GTG CTC
CTG TCC GGC CTC ATC GTC AAC GCC ATC CAG  V   V   L
 L   S   G   L   I   V   N   A   I   Q
        211/71
241/81  GCC GTC TTT GTG ACG ATA AGG CCC TTT
TCG AAG AGC TTC TAC CGT CGG ATC AAC AGA  A   V   F   V   T   I   R   P   F
 S   K   S   F   Y   R   R   I   N   R
271/91
        TTC TTG GCC GAG CTG TGG CTT CAG CTT
301/101 F   L   A   E   L   W   L   Q   L
GTC TGG GTG GAC TGG AAA GAG CAT GCA CAA GTA
 V   W   V   D   W   K   E   H   A   Q   V
        331/111
361/121 AAG GTA ATC ATA TCA AAT CAT CGG AGT GAT ATT GAT
TAC AGA TCA ATG GGT ATT TTG GCC CGG ATC  K   V   I   I   S   N   H   R   S   D   I   D
 Y   R   S   M   G   I   L   A   R   I
                391/131
421/141         ATC ATA
TGG CTC ATT GGA TGG ATA TTG CAG CGT GGG   I   I
 W   L   I   G   W   I   L   Q   R   G
                        451/151
481/161                 TCA ATG TGG TTT GCA GAG TAC
ATG AAG AAG TCA TCC AAG TTC CTT CCA GTT  S   M   W   F   A   E   Y
 M   K   K   S   S   K   F   L   P   V
                                511/171
541/181                         ATT GGC TGG TCA ATG TGG TTT GCA GAG TAC
CTC TTT TTG GAA AGG AGC TGG GCC AAG GAT  I   G   W   S   M   W   F   A   E   Y
 L   F   L   E   R   S   W   A   K   D
                                        571/191
                                        ACA CTA AAG TGG GGT CTC CAA AGG
                                         T   L   K   W   G   L   Q   R
```

FIG. 1A

```
601/201
TTG AAA GAC TTC CCT AGA CCA TTT TGG CTA                              631/211
 L   K   D   F   P   R   P   F   W   L   GCT CTT TTC GTC GAG GGT ACT CGC TTT ACT
661/221                                   A   L   F   V   E   G   T   R   F   T
CCA GCA AAG CTT CTC GCA GCT CAG GAA TAT
 P   A   K   L   L   A   A   Q   E   Y   691/231
721/241                                   GCG GCC TCC CAG GGC TTA CCG GCT CCT AGA
AAT GTA CTT ATT CCA CGT ACC AAG GGA TTT   A   A   S   Q   G   L   P   A   P   R
 N   V   L   I   P   R   T   K   G   F   751/251
781/261                                   GTA TCT GCT GTA AGT ATT ATG CGA GAT TTT
GTT CCA GCC ATT TAT GAT ACA ACT GTA ATA   V   S   A   V   S   I   M   R   D   F
 V   P   A   I   Y   D   T   T   V   I   811/271
841/281                                   GTC CCT AAA GAT TCC CAA AAA CCA ACA ATG
CTG CGG ATT TTG AAA GGG CAA TCA TCA GTG   V   P   K   D   S   Q   K   P   T   M
 L   R   I   L   K   G   Q   S   S   V   871/291
901/301                                   ATA CAT GTC CGC ATG AAA CGT CAT GCA ATG
AGT GAG ATG CCA AAA TCA GAT GAG GAT GTT   I   H   V   R   M   K   R   H   A   M
 S   E   M   P   K   S   D   E   D   V   931/311
961/331                                   TCA AAA TGG TGT AAA GAC ATT TTT GTG GCA
AAG GAT GCC TTA CTG GAC AAG CAT TTG GCA   S   K   W   C   K   D   I   F   V   A
 K   D   A   L   L   D   K   H   L   A   991/331
1021/341                                  ACA GGC ACT TTC GAT GAG GAG ATT AGA CCT
ATT GGC CGT CCA GTG AAA TCA TTG CTG GTG   T   G   T   F   D   E   E   I   R   P
 I   G   R   P   V   K   S   L   L   V   1051/351
1081/361                                  ACC CTG TTC TGG TCG TGC CTC CTG CTG TTT
GGC GCC ATC GAG TTC TTC AAG TGG ACA CAG   T   L   F   W   S   C   L   L   L   F
 G   A   I   E   F   F   K   W   T   Q   1111/371
                                          TCG ACG TGG AGG GGT GTG GCG TTC
                                           S   T   W   R   G   V   A   F
```

FIG. 1B

```
1141/381
ACT GCC GCA GGG ATG GCG CTT GTG ACG GGT GTC ATG CAT GTC TTC ATC ATG TTC TCC CAG
 T   A   A   G   M   A   L   V   T   G   V   M   H   V   F   I   M   F   S   Q
1201/401                                                           1171/391
GCT GAG CGG TCG AGC TCA GCC AGG GCG GCA CGG AAC CGG GTC AAG AAG GAA TGA AAA ATG
 A   E   R   S   S   S   A   R   A   A   R   N   R   V   K   K   E   *   K   M
1261/421                                          1231/411
GAG GGT GGA GAT GAG GTT CTC GTG GGG TTT GTT ATG GGC AAC CTT CAA AAG GAC TCT CCA
 E   G   G   D   E   V   L   V   G   F   V   M   G   N   L   Q   K   D   S   P
1321/441                         1291/431
TTC ATA TTA GTA TTA ATT CAT ATA TAT GCA GCG CCA AAT TCC AGA CAT TGA TAT GCT CTC
 F   I   L   V   L   I   H   I   Y   A   A   P   N   S   R   H   *   Y   A   L
1381/461              1351/451
AAA TAG GAT GTT CTG CTC CCC TCT TGT ATT TGT ATG CAG GAA AGG GTT TGT AGG GAG TTT
 K   *   D   V   L   L   P   S   C   I   C   M   Q   E   R   V   C   R   E   F
1441/481              1411/471
ACC CCC CCC CCC CCC CCC GCC TTT CTT TGG GgA AGA AAG ACA TaT TCT GGA AGC CTT
 T   P   P   P   P   P   A   F   L   W   G   R   K   T   Y   S   G   S   L
1501/501              1471/491
CCA GTA GTt CAA AA
 P   V   V   Q
```

FIG.1C

```
plsB  - Y F V E G G R S R T G R L L D -
          · · · · · · · ·     · ·
plsC  - M F P E G T R S R G R L L P -
          · · · · · ·     ·   · ·
maize - L F V E G T R F T P A K L L A -
        * + * + * * + * *       * *
```

FIG. 2

Maize = 374 aa vs. rape = 311 aa 51.5% identity; Optimized score: 705

```
maize     MAIPLVLVVLPLGLLFLLSGLIVNAIQAVLFVTIRPFSKSFYRRINRFLAELLWLQLVWV
          ::::  ::::::::::::::::
rape      MAMA-AAVIVPLGILFFISGLVVN------------------------------------
              10        20

10        20        30        40        50        60 maize     VDWWAGVKVQLHADEETYRSMGKEHALIISNHRSDIDWLIGWILAQRSGCLGSTLAVMKK
                                                  ::::::::::::  ::::::
rape      --------------------------------------LLQRSGCLGSALAVMKK
                                                         30        40

70        80        90       100       110       120 maize     SSKFLPVIGWSMWFAEYLFLERSWAKDEKTLKWGLQRLKDFPRPFWLALFVEGTRFTPAK
          ::::::::::::::: ::::::::::: ::::::  :::::: :::::::::::::::  ::
rape      SSKFLPVIGWSMWFSEYLFLERNWAKDESTLKSGLQRLNDFPRPFWLALFVEGTRFTEAK
                   50        60        70        80        90       100

```
maize  LLAAQEYAASQGLPAPRNVLIPRTKGFVSAVSIMRDFVPAIYDTTVIVPKDSPQPTMLRI
              190       200       210       220       230       240
       ::  :::::::  ::  ::::::::::::::  ::     :: :::::: :: ::
              110       120       130       140       150       160
rape   LKAAQEYAASSELPVPRNVLIPRTKGFVSAVSNMRSFVPAIYDMTVAIPKTSPPPTMLRL maize  LKGQSSVIHVRMKRHAMSEMPKSDEDVSKWCKDIFVAKDALLDKHLATGTF-DEEIRPIG
              250       260       270       280       290
       ::     ::::::             ::::::     :::::::: ::   .  ::
              170       180       190       200       210       220
rape   FRGQPSVVHVHIKCHSMKDLPESEDEIAQWCRDQFVTKDALLDKHIAADTFAGQKEQNIG maize  RPVKSLLVTLFWSCLLLFGAIEFFKWTQLLSTWRGVAFTAAGMALVTGVMHVFIMFSQAE
              300       310       320       330       340       350
       ::  :::  ::  ::   :::       ::: :::::::        ::::   ::::
              230       240       250       260       270       280
rape   RPIKSLAVVLSWACLLTLGAMKFLHWSNLFSSWKGIALSALGLGITLCMQILIRSSQSE maize  RSSSAARNRVKKE
              360       370
       ::   ::  :::
              290
rape   RSTPAKVAPAKPKDN

FIG. 5B
```

DNA ENCODING 2-ACYLTRANSFERASES

FIELD OF THE INVENTION

This invention relates to modified plants. In particular, the invention relates to plants modified such that at least part of the plant (for example seeds of the plant) is capable of yielding a commercially useful oil.

BACKGROUND OF THE INVENTION

Plants have long been a commercially valuable source of oil. Nutritional uses of plant-derived oils have hitherto been dominant, but attention is now turning additionally to plants as a source of industrially useful oils, for example as replacements for or improvements on mineral oils. Oil seeds, such as from rape, have a variety of lipids in them (Hildish & Williams, "Chemical Composition of Natural Lipids", Chapman Hall, London, 1964). There is now considerable interest in altering lipid composition by the use of recombinant DNA technology (Knauf, *TIBtech*, February 1987, 40–47), but by no means ail of the goals have been realised to date for a variety of reasons, in spite of the ever-increasing sophistication of the technology.

Success in tailoring the lipid content of plant-derived oils requires a firm understanding of the biochemistry and genes involved. Broadly, two approaches are available. First, plants may be modified to permit the synthesis of fatty acids which are new (for the plant); so, for example, laurate and/or stearate may be synthesised in rape. Secondly, the pattern and/or extent of incorporation of fatty acids into the glycerol backbone of the lipid may be altered. It is with this latter approach that the present invention is concerned, although the former approach may additionally be used.

Lipids are formed in plants by the addition of fatty acid moieties onto the glycerol backbone by a series of acyl transferase enzymes. There are three positions on the glycerol molecule at which fatty acid (acyl) moieties may be substituted, and the substitution reached at each position is catalysed by a position-specific enzyme: the enzymes are known as 1-, 2- and 3-acyltransferases, respectively.

One, but not the only, current aim of "lipid engineering" in plants is to provide oils including lipids with a high content of erucic (22:1) acid. Erucic acid-containing lipids are commercially desirable for a number of purposes, particularly as replacements to or supplements for mineral oils in certain circumstances, as alluded to above. In the case of oil seed rape (*Brassica napus*), one of the most significant oil producing crops in cultivation today, the specificity of the 2-acyltransferase enzyme positively discriminates against the incorporation of erucic acid at position 2. So, even in those cultivars of rape which are able to incorporate erucic acid at positions 1 and 3, where there is no (or at least reduced) discrimination against erucic acid, only a maximum 66% of the fatty acids incorporated into triacyl glycerols can be erucic acid. Such varieties of rape are known as HEAR (high erucic acid rape) varieties.

It would therefore be desirable to increase the erucic acid content of conventional oil seed rape, as well as HEAR varieties; the same can be said of oils of other vegetable oil crops such as maize, sunflower and soya, to name but a few examples. While in principle it may be thought possible to introduce into a desired plant DNA encoding a 2-acyltransferase of different fatty acid specificity, for example from a different plant, in practice there are a number of problems.

First, 2-acyltransferase and 3-acyltransferase are membrane bound, and therefore insoluble, enzymes. They have not been purified. This makes working with them difficult and rules out the use of many conventional DNA cloning procedures. This difficulty does not, paradoxically, lie in the way of cloning the gene (or at least cDNA) encoding the 1-acyltransferase enzyme, which is soluble: in fact, recombinant DNA work has already been undertaken on this enzyme for a completely different purpose, namely the enhancement of chilling resistance in tobacco plant leaves, by Murata et al (*Nature* 356 710–713 (1992)).

Secondly, very little is known about the 2- and 3-acyltransferases. There is no idea of their size or how they are targeted to membranes. No nucleotide or amino acid sequence data are available and no antibodies have been raised against them.

Although there has been discussion, therefore, of the desirability of modifying 2-acyltransferase specificity, for example by importing a gene coding for the corresponding enzyme, but of different specificity, from another species, there is a pressing need in the art for the key which enables this work to be done.

SUMMARY AND DETAILED DESCRIPTION OF THE INVENTION

The present invention provides such a key, in the form of a DNA sequence (in the specific case, a cDNA sequence) encoding a 2-acyltransferase. The DNA sequence in FIGS. 1A–1C (SEQ ID NO: 1) from nucleotides 130 to 1254 encodes the 2-acyltransferase from maize (*Zea mays*), including the stop codon.

According to a first aspect of the invention, therefore, there is provided a recombinant or isolated DNA sequence, preferably encoding an enzyme having membrane-bound acyltransferase activity, and selected from:

(i) a DNA sequence comprising the DNA sequence of FIGS. 1A–1C (SEQ ID NO: 1) encoding at least from $MET_1$ to $Stop_{375}$ (SEQ ID NO: 2) or its complementary strand, (ii) nucleic acid sequences hybridising to the DNA sequence of FIGS. 1A–1C (SEQ ID NO: 1), or its complementary strand, under stringent conditions, and (iii) nucleic acid sequences which would hybridise to the DNA sequence of FIGS. 1A–1C (SEQ ID NO: 1)(SEQ ID NO: 10), or its complementary strand, but for the degeneracy of the genetic code.

Fragments of the above DNA sequences, for example of at least 15, 20, 30, 40 or 60 nucleotides in length, are also within the scope of the invention.

Suitable stringent conditions include salt solutions of approximately 0.9 molar at temperatures of from 35° C. to 65° C. More particularly, stringent hybridisation conditions include 6× SSC, 5× Denhardt's solution, 0.5% SDS, 0.5% tetrasodium pyrophosphate and 50 μg/ml denatured herring sperm DNA; washing may be for 2×30 minutes at 65° C. in 1× SSC, 0.1% SDS and 1×30 minutes in 0.2× SSC, 0.1% SDS at 65° C.

Nucleic acid sequences within the scope of the first aspect of the invention will generally encode a protein having 2-acyltransferase activity, as that is the activity of the enzyme encoded by the nucleic acid sequence of FIGS. 1A–1C (SEQ ID NO: 1). Nucleic acid sequences not encoding a protein having enzymic activity (or the relevant enzymic activity) but otherwise conforming to the first aspect of the invention as set out above may be useful for other purposes (and are therefore also encompassed by the invention); for example they may be useful as probes, which is a utility shared by the nucleic acid sequences of the first aspect of the invention, including the FIG. 1 sequence itself.

The probe utility arises as follows. As there is likely to be a high degree of homology between acyltransferases of different species (and particularly between 2-acyltransferases of different species) the sequence of FIGS. 1A–1C (or part of it, or other sequences within the invention) may be used to probe cDNA or genomic libraries of other species in order to clone DNA sequences encoding acyltransferases having desired specificities. For example, if it is desired to produce oil having a high content of erucic acid esterified to glycerol, a DNA library of any species which naturally makes erucic acid may be probed. Suitable plants include meadow foam (Limnanthes spp., especially *L. alba* and, particularly, *L. douglassi*) and Crambe. *Limnanthes douglassi* is the preferred species, as specificity studies show that there is positive discrimination towards incorporation of erucic acid into position 2 of the triacylglyceride. Libraries of organisms other than the higher plants may be probed; for example, certain bacteria may have an acyltransferase of the desired specificity.

DNA in accordance with the invention will in general have a higher degree of homology with at least part of the sequence FIGS. 1A–1C (SEQ ID NO: 1) than with known sequences.

Recombinant DNA in accordance with the invention may be in the form of a vector, which may have sufficient regulatory sequences (such as a promoter) to direct expression. Vectors which are not expression vectors are useful for cloning purposes (as expression vectors themselves may be) . Host cells (such as bacteria and plant cells) containing vectors in accordance with the invention themselves form part of the invention.

DNA sequences in accordance with the invention can be used in another way in cloning a gene of interest from another species: if the DNA is coupled to a suitable promoter, for example on an expression vector in a suitable host organism, protein may be produced. Such protein may be used to generate polyclonal or monoclonal antibodies, or other binding molecules, which may then be used to screen for expression of homologous proteins in other species, for example as part of a DNA library screening programme.

Suitable CDNA libraries of target species will generally be prepared when the gene of interest is likely to be expressed; so cDNA embryo libraries (prepared at the early lipid synthesis stage), for example of Limnanthes spp. will be preferred.

The invention therefore enables the cloning of a wide variety of genes (or, more generally, DNA sequences) encoding acyltransferases, and 2-acyltransferases in particular, using DNA sequences as described above.

Such acyltransferases, such as from Limnanthes spp. may also be cloned directly, for example using complementation studies, from a DNA library of the species in question. For example, if *E. coli* is used as the complementation host, a mutant is chosen which is defective in the relevant enzyme (for example 2-acyltransferase); the DNA library from the target species (such as *L. douglassi*) is cloned into the mutant complementation host; host cells incorporating the target acyltransferase gene in their genome can readily be selected using appropriate selective media. *E. coli* mutant JC201 is a suitable host for use in complementation studies relating to 2-acyltransferase.

Cloning the acyltransferase gene of choice into a microbial host, such as a bacterium like *E. coli*, in such a way that the gene can be expressed has a particularly advantage in that the substrate specificity of the acyltransferase gene can be assessed in the microbial host before transformed plants are prepared, thereby saving considerably on research time.

Such an assessment may be made by competitive substrate assays, in which differently detectably labelled candidate substrates for the enzyme compete with each other for incorporation into the glyceride. For example, $^{14}C$-erucyl CoA and $^3H$-oleoyl CoA can be used as competitive substrates for 2-acyltransferase, and the relative amounts of $^{14}C$ or tritium uptake into glyceride can be measured. (As 2-acyltransferases have acceptor, glycerol-based, substrates and donor, fatty acid-based, substrates, the experiment can be carried out with different acceptors, such as 1-erucyl-glycerol-3-phosphate and 1-oleoyl-glycerol-3-phosphate.) A gene coding for an enzyme which preferentially donates erucic acid to the acceptor (particularly 1-erucyl-glycerol-3-phosphate) may by this means be identified as a DNA sequence of choice for further use in the invention as described below.

In a second aspect of the invention, there is provided a plant having one or more insoluble acyltransferase enzymes having a substrate specificity which differs from the native enzyme of the plant.

While site-directed mutagenesis and/or other protein engineering techniques may be used to alter the specificity of an enzyme native to the plant, it is preferred that the plant be transgenic and incorporate an expressible acyltransferase gene encoding an enzyme of the desired specificity from another species. 2-acyltransferases are the enzymes of choice. For example, as described above, a 2-acyltransferase enzyme which has an enhanced specificity for, or at least no discrimination against, erucic acid, may be made by this means to express in a plant which would not normally incorporate erucic acid into triacylglycerides. An important embodiment of the invention relates to genetically engineered plants which have higher levels of erucic acid incorporated into triacylglycerols than in corresponding non-engineered plants. Preferable though this embodiment may be, though, the invention is not limited to the enhancement of erucic acid incorporation into glycerides: other acids may be desired in other circumstances.

For the acyltransferase transgene to be expressible, a promoter has to be operatively coupled to it. Because at the present state of the art it is difficult precisely to regulate the site of incorporation of a transgene into the host genome, it is preferred that the transgene be coupled to its promoter prior to transformation of the plant. Promoters useful in the invention may be temporal- and/or seed-specific, but there is no need for them to be so: constitutive promoters, such as the CaMV 35S promoter, may be in fact be preferred because they are usually strong promoters. Other tissues are unlikely to be adversely affected if the transgene encoding the acyltransferase enzyme is expressed in them, as the availability of the fatty acid CoA substrates is effectively limited to the seed.

The promoter-transgene construct, once prepared, is introduced into plant cells by any suitable means. The invention extends to such plant cells. Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant or tissue culture containing the foreign DNA to be easily distinguished from other plants or tissue culture that do not contain the foreign DNA. Examples of such a marker gene include antibiotic resistance (Herrera-Estrella et al, *EMBO J.* 2(6) 987–95 (1983) and Herrera-Estrella et al, *Nature* 303 209–13 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods.

In one embodiment of the invention, the transgenic plant's native acyltransferase gene which corresponds to the transgene may be rendered at least partially inoperative or removed. So, if the transgene encodes a 2-acyltransferase, the plant's native 2-acyltransferase may be rendered inoperative by, for example, antisense or ribozyme techniques, as is known in the art.

By means of the invention, plants generating oil with a tailored lipid content may be produced. For example, the lipid composition of triacylglycerides in a plant may be substantially altered to produce triacylglycerides with a desired fatty acid (for example erucic acid) content higher than has hitherto been possible. For example, oil seed rape (*B. napus*) may be transformed to produce oil whose triacylglyceride has an erucic acid content of over 70%.

It can readily be seen that plants with increased lipid levels may be produced by means of the invention. However, the invention is also useful for producing plants with decreased lipid levels, which may be desired if elevated protein and/or starch levels are required. Decreased lipid levels may be achieved by interfering with the proper functioning of a gene encoding a 2-acyltransferase, for example by antisense or ribozyme technology. (Such reduced-lipid plants may if desired be further engineered for higher protein and/or starch content, if wished.)

Promoters which naturally drive 2-acyltransferases may also be obtained by hybridisation and/or restriction and/or sequencing studies using the sequence of FIGS. 1A–1C.

The invention enables the production of protein encoded by DNA of the first aspect of the invention, should that be desired. The protein may be expressed by host cells harbouring DNA in the form of an expression vector. The protein, which may be an enzyme having 2-acyltransferase activity, may have an amino acid sequence which is identical to or homologous with the sequence of FIGS. 1A–1C (SEQ ID NO: 2). The degree of homology will generally be greater than that of known proteins, and may be at least 40, 50, 60, 70, 80, 90, 95 or 99%.

Preferred features of each aspect of the invention are as for each other aspect mutatis mutandis.

BRIEF DESCRIPTION OF THE DRAWINGS

The invention is illustrated by the following examples. The examples refer to the accompanying drawings, in which:

FIGS. 1A–1C shows the cDNA sequence derived in Example 1 (SEQ ID NO: 1) and its derived protein sequence (SEQ ID NO: 2).

FIG. 2 shows a sequence alignment of part of the gene products of plsB (SEQ ID NO: 3) and plsC (SEQ ID NO: 4) with part of the sequence shown in FIGS. 1A–1C (SEQ ID NO: 5), showing a conserved motif. plsb is the *E. coli* sn-glycerol-3-phosphate acyltransferase gene and plsC the 1-acyl-sn-glycerol-3-phosphate acyltranserease gene of *E. coli*. Double points indicate exact matches between two sequences and a single point conservative amino acid substitutions. Stars indicate identical amino acids in all three sequences and residues conserved in two out of the three sequences are marked by a + symbol.

(FIG. 3B): JC201 containing the plasmid pPLSC, which encodes the *E. coli* 1-acyl-sn-glycerol-3-phosphate acyltransferase gene; (FIG. 3C): JC201 containing the plasmid whose cDNA insert sequence is shown in FIGS. 1A–1C. LPA, lysophosphatidic acid; PE, phosphatidylethanolamine; CL, cardiolipin; PG, phosphatidylglycerol; PA, phosphatidic acid; O, origin. 20% of the $^{32}$P is incorporated in LPA in JC201 and all of the corresponding label is incorporated in PE in both of the other two strains.

FIGS. 5A and 5B shows a comparison of the protein sequence shown in FIGS. 1A–1C (SEQ ID NO: 6) with that derived (SEQ ID NO: 7) from a *B. napus* seed cDNA insert which was isolated by DNA hybridisation to the maize cDNA sequence. The sequences were aligned with the FastA align program (1988). Double points signify identical amino acids and single points conservative amino acid substitutions.

Maize=374 aa vs. rape=311 aa 51.5% identity; Optimised score: 705

EXAMPLE 1

Derivation of the DNA sequence of FIGS. 1A–1C

Complementation studies using a maize cDNA expression library transferred into the *E. coli* mutant JC201 allowed the isolation of a plasmid encoding a 2-acyltransferase enzyme from maize. The cDNA insert of this plasmid is 1.6 kb in size, and includes a poly A tail of 70 bp. The insert was sequenced to give the data shown and translation of the sequence revealed the present of only one large open reading frame. This is shown on FIGS. 1A–1C with proposed start methionine and stop codon in bold print. The 2-acyltransferase is 374 amino acids in size and sequencing upstream of open reading from showed that the protein is expressed as part of a fusion protein in E. coli. This consists of 10 amino acids of the β-galactosidase protein, 43 amino acids (shown in sequence) corresponding to the 5' untranslated region of the MRNA and the 374 amino acid protein. Protein sequence comparisons of the large open reading frame with the 2-acyltransferase of E. coli show little overall identity but there is a stretch of 80 residues which has a high level of conservative substitution and contains some amino acids that are conserved in the 2-acyltransferase, 1-acyltransferase and N-acetyl glucosamine acyltransferase of E. coli.

EXAMPLE 2

Incorporation of 32p into total phospholipids

E. coli strains were grown in minimal medium containing $^{32}$P orthophosphate. Total glycerolipids were extracted into organic solvents and separated by 2D thin layer chromatography (FIG. 3) (Lysophosphatidic acid (LPA) is the substrate for 2-acyltransferase (2-AT)).

Figure 3A:
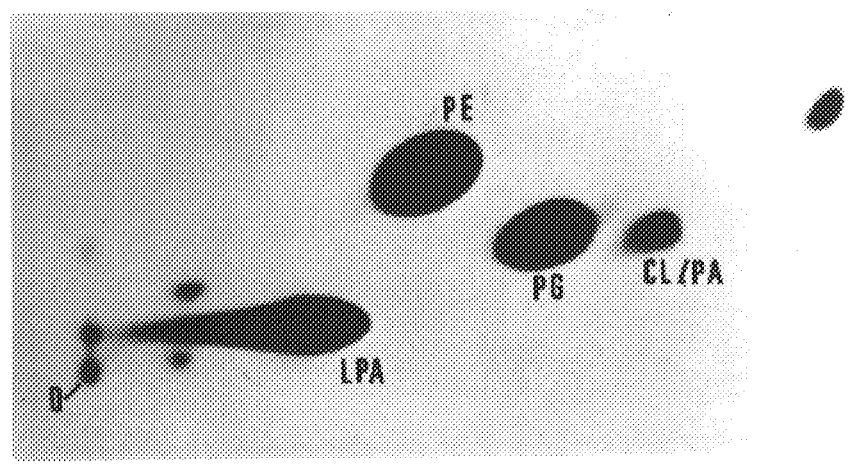
FIGS. 3A, 3B and 3C: Membrane phospholipids from *E. coli* strains were extracted into chloroform and separated by 2-dimensional thin layer chromatography. The first dimension (ascending) was developed using chloroform:methanol:water (65:25:4) and the second dimension (left to right) developed with chloroform:methanol:acetic acid (65:25:10). Phospholipids were visualised by autoradiography for 16 hours at −70° C. using Fuji RX film. The *E. coli* strains used were (FIG. 3A): JC201 which carries a thermosensitive mutation in the 1-acyl-sn-glycerol-3-phosphate acyltransferase gene.
Figure 3B:
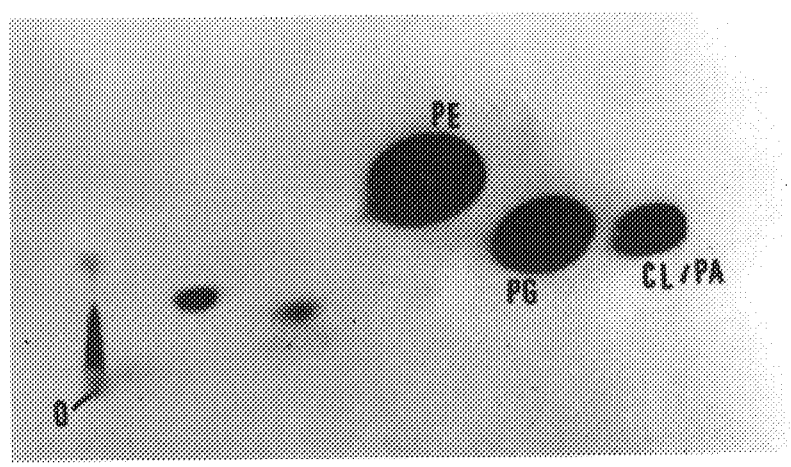
Figure 3C:
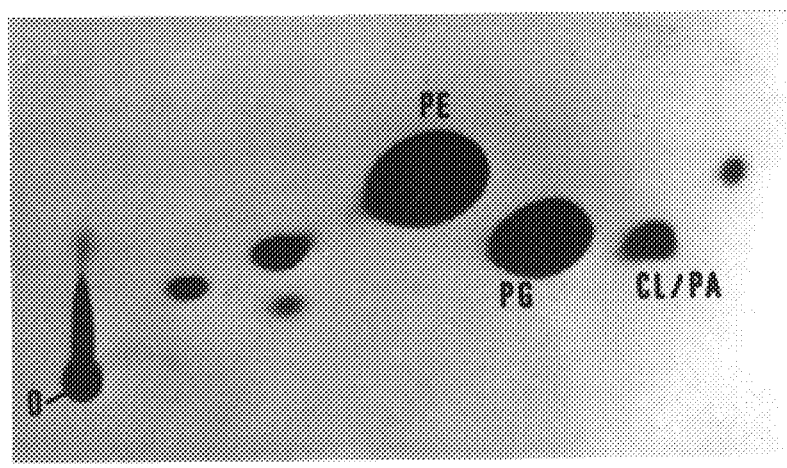

As can be seen in FIG. 3A, the accumulation of $^{32}$P-labelled LPA in the mutant JC 201 illustrates the absence of a fully functional 2-AT. Addition of a plasmid carrying either the native E. coli gene (FIG. 3B), or the maize clone given in FIGS. 1A–1C (FIG. 3C) restores 2-AT activity to the cells, allowing LPA to be removed and further metabolised. (Lysophosphatidic acid.)

These data indicate that the DNA sequence given in FIGS. 1A–1C codes for 2-AT.

EXAMPLE 3

Over expression of the cDNA

The cDNA region specifying the protein sequence given in FIGS. 1A–1C was cloned into the E. coli overexpression vector pET11d (Studier et al, Meth. Enzymol. 185 60–89 (1990)). Increased 2-acyltransferase activity following induction of expression from the plasmid insert confirmed that the sequence in FIGS. 1A–1C is that of 2-AT.

EXAMPLE 4

Figure 4:
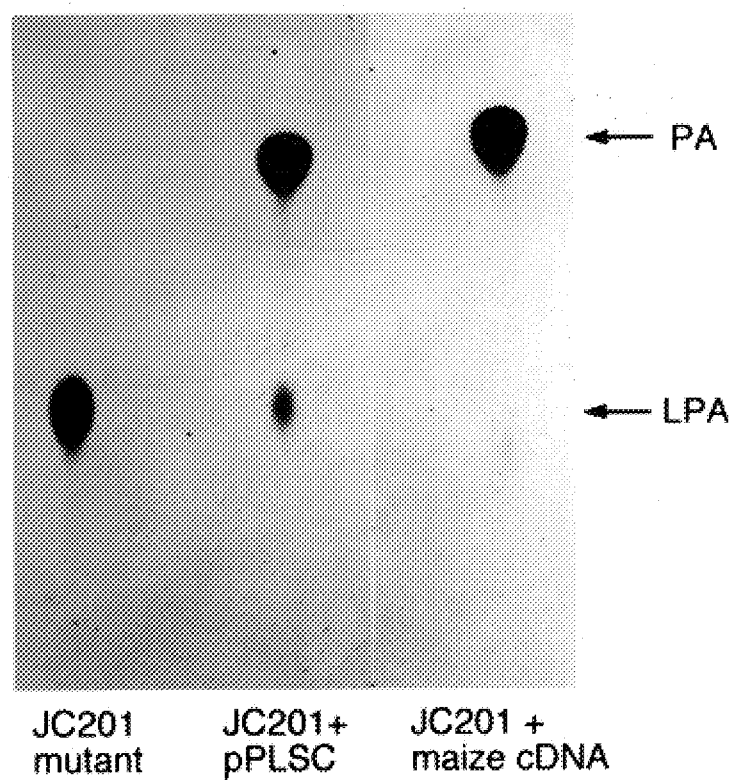
FIG. 4: Acyltransferase assays were performed using $^{32}$P-labelled lysophosphatidic acid which had been extracted from the *E. coli* strain JC201 and oleoyl CoA as an acyl donor. Phospholipids present in the reaction mixtures were extracted into chloroform and separated using silica gel thin layer chromatography. Chloroform:methanol:acetic acid:water (25:15:4:2) was used to develop the plates. The phospholipids were visualised by autoradiography for 16 hours at −70° C. using Fuji RX film. The *E. coli* strains used were: JC201 which carries a thermosensitive mutation in the 1-acyl-sn-glycerol-3-phosphate acyltransferase gene; JC201 containing the plasmid PPLSC which encodes the *E. coli* 1-acyl-sn-glycerol-3-phosphate acyltransferase gene; JC201 containing the plasmid whose maize cDNA insert sequence is shown in FIGS. 1A–1C. LPA, lysophosphatidic acid; PA, phosphatidic acid.

Localisation of 2-AT activity in E. coli cells containing the maize clone 2-acyltransferase assays were carried out using membranes isolated from the mutant strain JC.201 which lacks 2-AT and from JC.201 containing the maize plasmid (FIG. 4).

2-AT activity was not detected in membrane fractions from JC.201. The addition of a plasmid carrying the native E. coli gene or the sequence given in FIGS. 1A–1C (SEQ ID NO: 1), to JC.201 resulted in restoration of 2-AT activity to the membranes.

EXAMPLE 5

Using the maize cDNA as a heterologous probe to obtain cDNA from oilseed rape

A seed cDNA library from *Brassica napus* was screened with the sequence given in FIGS. 1A–1C (SEQ ID NO: 1), using standard techniques (Sambrook et al "Molecular Cloning—A Laboratory Manual", 2nd Edition, Cold Spring Harbor Laboratory Press, 1989).

Conditions

For the hybridisation of the maize cDNA insert to the rape library: hybridisation was in 6× SSC, 5× Denhardts solution, 0.5% SDS, 0.5% tetrasodium pyrophosphate and 50 ugml$^{-1}$ denatured herring sperm DNA. The filters were washed 2×30 minutes at 65° C. in 1× SSC, 0.1% SDS and 1×30 minutes in 0.2× SSC, 0.1% SDS at 65° C.

A hybridising clone was sequenced and a protein sequence derived for the large ORF. Alignment of this protein sequence with that derived from the maize cDNA clone given in FIGS. 1A–1C (SEQ ID NO: 1), is shown in FIGS. 5A and 5B.

The strong identity between these sequences illustrates the potential of using the sequence given in FIGS. 1A–1C (SEQ ID NO: 1) to obtain other 2-ATS.

EXAMPLE 6

Transgenic plants

The sequence given in FIGS. 1A–1C (SEQ ID NO: 1) can be cloned, alongside a suitable promoter, into a suitable vector for expression in plants. The vector can be used to transform plants and the resulting plants expressing the 2-AT can be analysed for lipid content. Lipid metabolism is expected to be upregulated and elevated lipid levels were detectable in seeds.

EXAMPLE 7

Antisense

The sequence given in FIGS. 1A–1C (SEQ ID NO: 1) may be cloned, alongside a suitable promoter, in the antisense orientation into a suitable vector for expression in plants. The vector can be used to transform plants and the resulting plants expressing the 2-AT can be analysed for protein and starch content. Elevated levels of starch and protein are expected to be detectable in seeds.

EXAMPLE 8

Down-regulation of Native 2-AT

The DNA sequence of a 2-AT derived from *L. douglassii* (obtained as described in Example 5) can be introduced into oilseed rape (OSR) under the expression of a suitable promoter, using vectors and plant transformation methods well known in the art. A second sequence, comprising antisense or ribozymes against the rape cDNA (Example 5) can be introduced for simultaneous expression. The resultant transformed plant is expected to have 2-AT activity corresponding to that of *L. douglassii*, with concurrent down regulation of the native rape 2-AT gene.

The modified OSR plant thus obtained had higher levels of erucic acid in position 2 of its triacylglycerols than wild type plants. In addition higher levels of trierucin are found in the seed oil.

EXAMPLE 9

Genomic library screening

The sequence given in FIGS. 1A–1C (SEQ ID NO: 1) is used to screen a genomic library of Arabidopsis and a hybrid using clone obtained. Using standard techniques, a promoter may be derived from this clone. The promoter may be used to drive expression in plant cell membranes.

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
( A ) LENGTH: 1514 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 130..1254

( x i ) SEQUENCE DESCRIPTION: SEQ ID NO: 1:

```
CCCCGTCCTC  CTCGTCGCCG  GCGGAGCCGC  CTACTATCGC  CTGGAGAAGG  AGCGCCGCGG        60

GGAGCTTTTC  CCACTGCCGA  CTGCCGTCTG  ACCCTCCGAG  ATCGGAAGCG  GCGCCGGCGC      120

CGGCCGGCG  ATG  GCG  ATC  CCG  CTC  GTG  CTC  GTC  GTG  CTC  CCG  CTC  GGC    168
           Met  Ala  Ile  Pro  Leu  Val  Leu  Val  Val  Leu  Pro  Leu  Gly
            1                5                    10

CTG  CTC  TTC  CTC  CTG  TCC  GGC  CTC  ATC  GTC  AAC  GCC  ATC  CAG  GCC  GTC    216
Leu  Leu  Phe  Leu  Leu  Ser  Gly  Leu  Ile  Val  Asn  Ala  Ile  Gln  Ala  Val
     15                  20                       25

CTA  TTT  GTG  ACG  ATA  AGG  CCC  TTT  TCG  AAG  AGC  TTC  TAC  CGT  CGG  ATC    264
Leu  Phe  Val  Thr  Ile  Arg  Pro  Phe  Ser  Lys  Ser  Phe  Tyr  Arg  Arg  Ile
 30                      35                       40                       45

AAC  AGA  TTC  TTG  GCC  GAG  CTG  CTG  TGG  CTT  CAG  CTT  GTC  TGG  GTG  GTG    312
Asn  Arg  Phe  Leu  Ala  Glu  Leu  Leu  Trp  Leu  Gln  Leu  Val  Trp  Val  Val
                      50                       55                   60

GAC  TGG  TGG  GCA  GGT  GTT  AAG  GTA  CAA  CTG  CAT  GCA  GAT  GAG  GAA  ACT    360
Asp  Trp  Trp  Ala  Gly  Val  Lys  Val  Gln  Leu  His  Ala  Asp  Glu  Glu  Thr
                      65                       70                   75

TAC  AGA  TCA  ATG  GGT  AAA  GAG  CAT  GCA  CTC  ATC  ATA  TCA  AAT  CAT  CGG    408
Tyr  Arg  Ser  Met  Gly  Lys  Glu  His  Ala  Leu  Ile  Ile  Ser  Asn  His  Arg
              80                       85                   90

AGT  GAT  ATT  GAT  TGG  CTC  ATT  GGA  TGG  ATA  TTG  GCC  CAG  CGT  TCA  GGG    456
Ser  Asp  Ile  Asp  Trp  Leu  Ile  Gly  Trp  Ile  Leu  Ala  Gln  Arg  Ser  Gly
     95                      100                      105

TGC  CTT  GGA  AGT  ACA  CTT  GCT  GTC  ATG  AAG  AAG  TCA  TCC  AAG  TTC  CTT    504
Cys  Leu  Gly  Ser  Thr  Leu  Ala  Val  Met  Lys  Lys  Ser  Ser  Lys  Phe  Leu
110                      115                      120                     125

CCA  GTT  ATT  GGC  TGG  TCA  ATG  TGG  TTT  GCA  GAG  TAC  CTC  TTT  TTG  GAA    552
Pro  Val  Ile  Gly  Trp  Ser  Met  Trp  Phe  Ala  Glu  Tyr  Leu  Phe  Leu  Glu
                     130                      135                      140

AGG  AGC  TGG  GCC  AAG  GAT  GAA  AAG  ACA  CTA  AAG  TGG  GGT  CTC  CAA  AGG    600
Arg  Ser  Trp  Ala  Lys  Asp  Glu  Lys  Thr  Leu  Lys  Trp  Gly  Leu  Gln  Arg
               145                      150                      155

TTG  AAA  GAC  TTC  CCT  AGA  CCA  TTT  TGG  CTA  GCT  CTT  TTC  GTC  GAG  GGT    648
Leu  Lys  Asp  Phe  Pro  Arg  Pro  Phe  Trp  Leu  Ala  Leu  Phe  Val  Glu  Gly
               160                      165                      170

ACT  CGC  TTT  ACT  CCA  GCA  AAG  CTT  CTC  GCA  GCT  CAG  GAA  TAT  GCG  GCC    696
Thr  Arg  Phe  Thr  Pro  Ala  Lys  Leu  Leu  Ala  Ala  Gln  Glu  Tyr  Ala  Ala
      175                      180                      185

TCC  CAG  GGC  TTA  CCG  GCT  CCT  AGA  AAT  GTA  CTT  ATT  CCA  CGT  ACC  AAG    744
Ser  Gln  Gly  Leu  Pro  Ala  Pro  Arg  Asn  Val  Leu  Ile  Pro  Arg  Thr  Lys
190                      195                      200                     205
```

| | | | | | | | | | | | | | | | | |
|---|---|---|---|---|---|---|---|---|---|---|---|---|---|---|---|---|
| GGA | TTT | GTA | TCT | GCT | GTA | AGT | ATT | ATG | CGA | GAT | TTT | GTT | CCA | GCC | ATT | 792 |
| Gly | Phe | Val | Ser | Ala | Val | Ser | Ile | Met | Arg | Asp | Phe | Val | Pro | Ala | Ile | |
| | | | 210 | | | | | 215 | | | | | 220 | | | |
| TAT | GAT | ACA | ACT | GTA | ATA | GTC | CCT | AAA | GAT | TCC | CCT | CAA | CCA | ACA | ATG | 840 |
| Tyr | Asp | Thr | Thr | Val | Ile | Val | Pro | Lys | Asp | Ser | Pro | Gln | Pro | Thr | Met | |
| | | | 225 | | | | 230 | | | | | 235 | | | | |
| CTG | CGG | ATT | TTG | AAA | GGG | CAA | TCA | TCA | GTG | ATA | CAT | GTC | CGC | ATG | AAA | 888 |
| Leu | Arg | Ile | Leu | Lys | Gly | Gln | Ser | Ser | Val | Ile | His | Val | Arg | Met | Lys | |
| | | 240 | | | | | 245 | | | | | 250 | | | | |
| CGT | CAT | GCA | ATG | AGT | GAG | ATG | CCA | AAA | TCA | GAT | GAG | GAT | GTT | TCA | AAA | 936 |
| Arg | His | Ala | Met | Ser | Glu | Met | Pro | Lys | Ser | Asp | Glu | Asp | Val | Ser | Lys | |
| | 255 | | | | 260 | | | | | 265 | | | | | | |
| TGG | TGT | AAA | GAC | ATT | TTT | GTG | GCA | AAG | GAT | GCC | TTA | CTG | GAC | AAG | CAT | 984 |
| Trp | Cys | Lys | Asp | Ile | Phe | Val | Ala | Lys | Asp | Ala | Leu | Leu | Asp | Lys | His | |
| 270 | | | | 275 | | | | 280 | | | | | 285 | | | |
| TTG | GCA | ACA | GGC | ACT | TTC | GAT | GAG | GAG | ATT | AGA | CCT | ATT | GGC | CGT | CCA | 1032 |
| Leu | Ala | Thr | Gly | Thr | Phe | Asp | Glu | Glu | Ile | Arg | Pro | Ile | Gly | Arg | Pro | |
| | | | | 290 | | | | 295 | | | | | 300 | | | |
| GTG | AAA | TCA | TTG | CTG | GTG | ACC | CTG | TTC | TGG | TCG | TGC | CTC | CTG | CTG | TTT | 1080 |
| Val | Lys | Ser | Leu | Leu | Val | Thr | Leu | Phe | Trp | Ser | Cys | Leu | Leu | Leu | Phe | |
| | | | 305 | | | | | 310 | | | | | 315 | | | |
| GGC | GCC | ATC | GAG | TTC | TTC | AAG | TGG | ACA | CAG | CTT | CTG | TCG | ACG | TGG | AGG | 1128 |
| Gly | Ala | Ile | Glu | Phe | Phe | Lys | Trp | Thr | Gln | Leu | Leu | Ser | Thr | Trp | Arg | |
| | | 320 | | | | | 325 | | | | | 330 | | | | |
| GGT | GTG | GCG | TTC | ACT | GCC | GCA | GGG | ATG | GCG | CTT | GTG | ACG | GGT | GTC | ATG | 1176 |
| Gly | Val | Ala | Phe | Thr | Ala | Ala | Gly | Met | Ala | Leu | Val | Thr | Gly | Val | Met | |
| | 335 | | | | | 340 | | | | | 345 | | | | | |
| CAT | GTC | TTC | ATC | ATG | TTC | TCC | CAG | GCT | GAG | CGG | TCG | AGC | TCA | GCC | AGG | 1224 |
| His | Val | Phe | Ile | Met | Phe | Ser | Gln | Ala | Glu | Arg | Ser | Ser | Ser | Ala | Arg | |
| 350 | | | | | 355 | | | | 360 | | | | | 365 | | |
| GCG | GCA | CGG | AAC | CGG | GTC | AAG | AAG | GAA | TGAAAAATGG | | AGGGTGGAGA | | | | | 1271 |
| Ala | Ala | Arg | Asn | Arg | Val | Lys | Lys | Glu | | | | | | | | |
| | | | | 370 | | | | 375 | | | | | | | | |
| TGAGGTTCTC | GTGGGGTTTG | TTATGGGCAA | CCTTCAAAAG | GACTCTCCAT | TCATATTAGT | | | | | | | | | | | 1331 |
| ATTAATTCAT | ATATATGCAG | CGCCAAATTC | CAGACATTGA | TATGCTCTCA | AATAGGATGT | | | | | | | | | | | 1391 |
| TCTGCTCCCC | TCTTGTATTT | GTATGCAGGA | AAGGGTTTGT | AGGGAGTTTA | CCCCCCCCCC | | | | | | | | | | | 1451 |
| CCCCCCCCCC | GCCTTTCTTT | GGGGAAGAAA | GACATATTCT | GGAAGCCTTC | CAGTAGTTCA | | | | | | | | | | | 1511 |
| AAA | | | | | | | | | | | | | | | | 1514 |

( 2 ) INFORMATION FOR SEQ ID NO: 2:

( i ) SEQUENCE CHARACTERISTICS:
        ( A ) LENGTH: 374 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Ala | Ile | Pro | Leu | Val | Leu | Val | Val | Leu | Pro | Leu | Gly | Leu | Leu | Phe |
| 1 | | | | 5 | | | | | 10 | | | | | 15 | |
| Leu | Leu | Ser | Gly | Leu | Ile | Val | Asn | Ala | Ile | Gln | Ala | Val | Leu | Phe | Val |
| | | | 20 | | | | | 25 | | | | | 30 | | |
| Thr | Ile | Arg | Pro | Phe | Ser | Lys | Ser | Phe | Tyr | Arg | Arg | Ile | Asn | Arg | Phe |
| | | 35 | | | | | 40 | | | | | 45 | | | |
| Leu | Ala | Glu | Leu | Leu | Trp | Leu | Gln | Leu | Val | Trp | Val | Val | Asp | Trp | Trp |
| | 50 | | | | | 55 | | | | | 60 | | | | |
| Ala | Gly | Val | Lys | Val | Gln | Leu | His | Ala | Asp | Glu | Glu | Thr | Tyr | Arg | Ser |
| 65 | | | | | 70 | | | | | 75 | | | | | 80 |

```
Met  Gly  Lys  Glu  His  Ala  Leu  Ile  Ile  Ser  Asn  His  Arg  Ser  Asp  Ile
               85                       90                       95

Asp  Trp  Leu  Ile  Gly  Trp  Ile  Leu  Ala  Gln  Arg  Ser  Gly  Cys  Leu  Gly
               100                      105                      110

Ser  Thr  Leu  Ala  Val  Met  Lys  Lys  Ser  Ser  Lys  Phe  Leu  Pro  Val  Ile
               115                      120                      125

Gly  Trp  Ser  Met  Trp  Phe  Ala  Glu  Tyr  Leu  Phe  Leu  Glu  Arg  Ser  Trp
          130                      135                      140

Ala  Lys  Asp  Glu  Lys  Thr  Leu  Lys  Trp  Gly  Leu  Gln  Arg  Leu  Lys  Asp
145                      150                      155                      160

Phe  Pro  Arg  Pro  Phe  Trp  Leu  Ala  Leu  Phe  Val  Glu  Gly  Thr  Arg  Phe
               165                      170                      175

Thr  Pro  Ala  Lys  Leu  Leu  Ala  Ala  Gln  Glu  Tyr  Ala  Ala  Ser  Gln  Gly
               180                      185                      190

Leu  Pro  Ala  Pro  Arg  Asn  Val  Leu  Ile  Pro  Arg  Thr  Lys  Gly  Phe  Val
               195                      200                      205

Ser  Ala  Val  Ser  Ile  Met  Arg  Asp  Phe  Val  Pro  Ala  Ile  Tyr  Asp  Thr
          210                      215                      220

Thr  Val  Ile  Val  Pro  Lys  Asp  Ser  Pro  Gln  Pro  Thr  Met  Leu  Arg  Ile
225                      230                      235                      240

Leu  Lys  Gly  Gln  Ser  Ser  Val  Ile  His  Val  Arg  Met  Lys  Arg  His  Ala
               245                      250                      255

Met  Ser  Glu  Met  Pro  Lys  Ser  Asp  Glu  Asp  Val  Ser  Lys  Trp  Cys  Lys
               260                      265                      270

Asp  Ile  Phe  Val  Ala  Lys  Asp  Ala  Leu  Leu  Asp  Lys  His  Leu  Ala  Thr
          275                      280                      285

Gly  Thr  Phe  Asp  Glu  Glu  Ile  Arg  Pro  Ile  Gly  Arg  Pro  Val  Lys  Ser
     290                      295                      300

Leu  Leu  Val  Thr  Leu  Phe  Trp  Ser  Cys  Leu  Leu  Leu  Phe  Gly  Ala  Ile
305                      310                      315                      320

Glu  Phe  Phe  Lys  Trp  Thr  Gln  Leu  Leu  Ser  Thr  Trp  Arg  Gly  Val  Ala
               325                      330                      335

Phe  Thr  Ala  Ala  Gly  Met  Ala  Leu  Val  Thr  Gly  Val  Met  His  Val  Phe
               340                      345                      350

Ile  Met  Phe  Ser  Gln  Ala  Glu  Arg  Ser  Ser  Ser  Ala  Arg  Ala  Ala  Arg
               355                      360                      365

Asn  Arg  Val  Lys  Lys  Glu
               370
```

( 2 ) INFORMATION FOR SEQ ID NO: 3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

```
Tyr  Phe  Val  Glu  Gly  Gly  Arg  Ser  Arg  Thr  Gly  Arg  Leu  Leu  Asp
1              5                        10                            15
```

( 2 ) INFORMATION FOR SEQ ID NO: 4:

( i ) SEQUENCE CHARACTERISTICS:
        ( A ) LENGTH: 15 amino acids
        ( B ) TYPE: amino acid
        ( D ) TOPOLOGY: linear (  i  i  ) MOLECULE TYPE: protein ( x i ) SEQUENCE DESCRIPTION: SEQ ID NO: 4:

| Met | Phe | Pro | Glu | Thr | Arg | Ser | Arg | Gly | Arg | Gly | Leu | Leu | Pro |
|-----|-----|-----|-----|-----|-----|-----|-----|-----|-----|-----|-----|-----|-----|
| 1   |     |     |     | 5   |     |     |     |     | 10  |     |     |     | 15  |

( 2 ) INFORMATION FOR SEQ ID NO: 5:

( i ) SEQUENCE CHARACTERISTICS:
       ( A ) LENGTH: 15 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 5:

Leu Phe Val Glu Gly Thr Arg Phe Thr Pro Ala Lys Leu Leu Ala
1               5                   10                  15

( 2 ) INFORMATION FOR SEQ ID NO: 6:

( i ) SEQUENCE CHARACTERISTICS:
       ( A ) LENGTH: 374 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 6:

Met Ala Ile Pro Leu Val Leu Val Val Leu Pro Leu Gly Leu Leu Phe
1               5                   10                  15

Leu Leu Ser Gly Leu Ile Val Asn Ala Ile Gln Ala Val Leu Phe Val
                20                  25                  30

Thr Ile Arg Pro Phe Ser Lys Ser Phe Tyr Arg Arg Ile Asn Arg Phe
            35                  40                  45

Leu Ala Glu Leu Leu Trp Leu Gln Leu Val Trp Val Asp Trp Trp
        50                  55                  60

Ala Gly Val Lys Val Gln Leu His Ala Asp Glu Thr Tyr Arg Ser
65                  70                  75                  80

Met Gly Lys Glu His Ala Leu Ile Ile Ser Asn His Arg Ser Asp Ile
                85                  90                  95

Asp Trp Leu Ile Gly Trp Ile Leu Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
    130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
                165                 170                 175

Thr Pro Ala Lys Leu Leu Ala Ala Gln Glu Tyr Ala Ala Ser Gln Gly
            180                 185                 190

Leu Pro Ala Pro Arg Asn Val Leu Ile Pro Arg Thr Lys Gly Phe Val
        195                 200                 205

Ser Ala Val Ser Ile Met Arg Asp Phe Val Pro Ala Ile Tyr Asp Thr
    210                 215                 220

Thr Val Ile Val Pro Lys Asp Ser Pro Gln Pro Thr Met Leu Arg Ile
225                 230                 235                 240

|     |     |     |     |     |     |     |     |     |     |     |     |     |     |     |
|---|---|---|---|---|---|---|---|---|---|---|---|---|---|---|
| Leu | Lys | Gly | Gln | Ser | Ser | Val | Ile | His | Val | Arg | Met | Lys | Arg | His | Ala |
|  |  |  |  | 245 |  |  |  | 250 |  |  |  |  | 255 |  |

| Met | Ser | Glu | Met | Pro | Lys | Ser | Asp | Glu | Asp | Val | Ser | Lys | Trp | Cys | Lys |
|---|---|---|---|---|---|---|---|---|---|---|---|---|---|---|---|
|  |  |  | 260 |  |  |  | 265 |  |  |  |  |  | 270 |  |  |

| Asp | Ile | Phe | Val | Ala | Lys | Asp | Ala | Leu | Leu | Asp | Lys | His | Leu | Ala | Thr |
|---|---|---|---|---|---|---|---|---|---|---|---|---|---|---|---|
|  |  | 275 |  |  |  |  | 280 |  |  |  |  | 285 |  |  |  |

| Gly | Thr | Phe | Asp | Glu | Glu | Ile | Arg | Pro | Ile | Gly | Arg | Pro | Val | Lys | Ser |
|---|---|---|---|---|---|---|---|---|---|---|---|---|---|---|---|
|  | 290 |  |  |  |  | 295 |  |  |  |  | 300 |  |  |  |  |

| Leu | Leu | Val | Thr | Leu | Phe | Trp | Ser | Cys | Leu | Leu | Leu | Phe | Gly | Ala | Ile |
|---|---|---|---|---|---|---|---|---|---|---|---|---|---|---|---|
| 305 |  |  |  |  | 310 |  |  |  |  | 315 |  |  |  |  | 320 |

| Glu | Phe | Phe | Lys | Trp | Thr | Gln | Leu | Leu | Ser | Thr | Trp | Arg | Gly | Val | Ala |
|---|---|---|---|---|---|---|---|---|---|---|---|---|---|---|---|
|  |  |  |  | 325 |  |  |  |  | 330 |  |  |  |  | 335 |  |

| Phe | Thr | Ala | Ala | Gly | Met | Ala | Leu | Val | Thr | Gly | Val | Met | His | Val | Phe |
|---|---|---|---|---|---|---|---|---|---|---|---|---|---|---|---|
|  |  |  | 340 |  |  |  |  | 345 |  |  |  |  | 350 |  |  |

| Ile | Met | Phe | Ser | Gln | Ala | Glu | Arg | Ser | Ser | Ser | Ala | Arg | Ala | Ala | Arg |
|---|---|---|---|---|---|---|---|---|---|---|---|---|---|---|---|
|  |  | 355 |  |  |  |  | 360 |  |  |  |  | 365 |  |  |  |

| Asn | Arg | Val | Lys | Lys | Glu |
|---|---|---|---|---|---|
| 370 |  |  |  |  |  |

( 2 ) INFORMATION FOR SEQ ID NO: 7:

( i ) SEQUENCE CHARACTERISTICS:
      ( A ) LENGTH: 295 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 7:

| Met | Ala | Met | Ala | Ala | Ala | Val | Ile | Val | Pro | Leu | Gly | Ile | Leu | Phe | Phe |
|---|---|---|---|---|---|---|---|---|---|---|---|---|---|---|---|
| 1 |  |  |  | 5 |  |  |  |  | 10 |  |  |  |  | 15 |  |

| Ile | Ser | Gly | Leu | Val | Val | Asn | Leu | Leu | Gln | Arg | Ser | Gly | Cys | Leu | Gly |
|---|---|---|---|---|---|---|---|---|---|---|---|---|---|---|---|
|  |  |  | 20 |  |  |  |  | 25 |  |  |  |  | 30 |  |  |

| Ser | Ala | Leu | Ala | Val | Met | Lys | Lys | Ser | Ser | Lys | Phe | Leu | Pro | Val | Ile |
|---|---|---|---|---|---|---|---|---|---|---|---|---|---|---|---|
|  |  |  | 35 |  |  |  | 40 |  |  |  |  | 45 |  |  |  |

| Gly | Trp | Ser | Met | Trp | Phe | Ser | Glu | Tyr | Leu | Phe | Leu | Glu | Arg | Asn | Trp |
|---|---|---|---|---|---|---|---|---|---|---|---|---|---|---|---|
|  | 50 |  |  |  |  | 55 |  |  |  |  | 60 |  |  |  |  |

| Ala | Lys | Asp | Glu | Ser | Thr | Leu | Lys | Ser | Gly | Leu | Gln | Arg | Leu | Asn | Asp |
|---|---|---|---|---|---|---|---|---|---|---|---|---|---|---|---|
| 65 |  |  |  |  | 70 |  |  |  |  | 75 |  |  |  |  | 80 |

| Phe | Pro | Arg | Pro | Phe | Trp | Leu | Ala | Leu | Phe | Val | Glu | Gly | Thr | Arg | Phe |
|---|---|---|---|---|---|---|---|---|---|---|---|---|---|---|---|
|  |  |  |  | 85 |  |  |  |  | 90 |  |  |  |  | 95 |  |

| Thr | Glu | Ala | Lys | Leu | Lys | Ala | Ala | Gln | Glu | Tyr | Ala | Ala | Ser | Ser | Glu |
|---|---|---|---|---|---|---|---|---|---|---|---|---|---|---|---|
|  |  |  | 100 |  |  |  |  | 105 |  |  |  |  | 110 |  |  |

| Leu | Pro | Val | Pro | Arg | Asn | Val | Leu | Ile | Pro | Arg | Thr | Lys | Gly | Phe | Val |
|---|---|---|---|---|---|---|---|---|---|---|---|---|---|---|---|
|  |  | 115 |  |  |  |  | 120 |  |  |  |  | 125 |  |  |  |

| Ser | Ala | Val | Ser | Asn | Met | Arg | Ser | Phe | Val | Pro | Ala | Ile | Tyr | Asp | Met |
|---|---|---|---|---|---|---|---|---|---|---|---|---|---|---|---|
|  | 130 |  |  |  |  | 135 |  |  |  |  | 140 |  |  |  |  |

| Thr | Val | Ala | Ile | Pro | Lys | Thr | Ser | Pro | Pro | Thr | Met | Leu | Arg | Leu |
|---|---|---|---|---|---|---|---|---|---|---|---|---|---|---|
| 145 |  |  |  |  | 150 |  |  |  |  | 155 |  |  |  | 160 |

| Phe | Lys | Gly | Gln | Pro | Ser | Val | Val | His | Val | His | Ile | Lys | Cys | His | Ser |
|---|---|---|---|---|---|---|---|---|---|---|---|---|---|---|---|
|  |  |  |  | 165 |  |  |  |  | 170 |  |  |  |  | 175 |  |

| Met | Lys | Asp | Leu | Pro | Glu | Ser | Glu | Asp | Glu | Ile | Ala | Gln | Trp | Cys | Arg |
|---|---|---|---|---|---|---|---|---|---|---|---|---|---|---|---|
|  |  |  | 180 |  |  |  |  | 185 |  |  |  |  | 190 |  |  |

| Asp | Gln | Phe | Val | Thr | Lys | Asp | Ala | Leu | Leu | Asp | Lys | His | Ile | Ala | Ala |
|---|---|---|---|---|---|---|---|---|---|---|---|---|---|---|---|
|  |  | 195 |  |  |  |  | 200 |  |  |  |  | 205 |  |  |  |

| Asp | Thr | Phe | Ala | Gly | Gln | Lys | Glu | Gln | Asn | Ile | Gly | Arg | Pro | Ile | Lys |
|---|---|---|---|---|---|---|---|---|---|---|---|---|---|---|---|
|  | 210 |  |  |  |  | 215 |  |  |  |  | 220 |  |  |  |  |

-continued

| Ser 225 | Leu | Ala | Val | Val | Leu 230 | Ser | Trp | Ala | Cys | Leu 235 | Leu | Thr | Leu | Gly | Ala 240 |
| Met | Lys | Phe | Leu | His 245 | Trp | Ser | Asn | Leu | Phe 250 | Ser | Ser | Trp | Lys | Gly 255 | Ile |
| Ala | Leu | Ser | Ala 260 | Leu | Gly | Leu | Gly | Ile 265 | Ile | Thr | Leu | Cys | Met 270 | Gln | Ile |
| Leu | Ile | Arg 275 | Ser | Ser | Gln | Ser | Glu 280 | Arg | Ser | Thr | Pro | Ala 285 | Lys | Val | Ala |
| Pro | Ala 290 | Lys | Pro | Lys | Asp | Asn 295 | | | | | | | | | |

We claim:

1. A recombinant or isolated nucleic acid molecule comprising a polynucleotide sequence selected from the group consisting of
   (a) a nucleotide sequence encoding the polypeptide having the amino acid sequence in FIGS. 1A–1C (SEQ ID NO: 2) from about amino acid 1 to about amino acid 374 in SEQ ID NO: 2
   (b) a nucleotide sequence complementary to a nucleotide sequence encoding the polypeptide having the amino acid sequence in FIGS. 1A–1C (SEQ ID NO: 2) from about amino acid 1 to about amino acid 374 in SEQ ID NO: 2;
   (c) a nucleotide sequence which hybridizes to the nucleotide sequence in FIGS. 1A–1C (SEQ ID NO: 1) under stringent conditions; and
   (d) a nucleotide sequence which hybridizes to the nucleotide sequence that is complementary to the nucleotide sequence in FIGS. 1A–1C (SEQ ID NO: 1) under stringent conditions.

2. The nucleic acid molecule according to claim 1, wherein said polynucleotide sequence encodes an enzyme having membrane-bound acyltransferase activity.

3. The nucleic acid molecule according to claim 2, wherein said acyltransferase activity is 2-acyltransferase activity.

4. A microbial host capable of expressing a polynucleotide according to claim 1.

5. A fragment of said polynucleotide according to claim 1 said fragment comprising at least 15 nucleotides.

6. A nucleotide sequence encoding an RNA, said RNA being in antisense orientation to the RNA encoded by the polynucleotide according to claim 1.

7. A method for making a recombinant vector comprising inserting an isolated nucleic acid molecule according to claim 1 into a vector.

8. The nucleic acid molecule according to claim 1, wherein said polynucleotide has the complete nucleotide sequence in FIGS. 1A–1C (SEQ ID NO: 1).

9. The nucleic acid molecule according to claim 1, wherein said polynucleotide has the nucleotide sequence in FIGS. 1A–1C (SEQ ID NO: 1) encoding the polypeptide having the amino acid sequence in FIGS. 1A–1C (SEQ ID NO: 2) from about amino acid 1 to about amino acid 375.

10. A recombinant vector produced by the method according to claim 7.

11. The recombinant vector according to claim 10, wherein said vector is an expression vector containing a promoter which drives the expression of said nucleic acid molecule.

12. A method of making a host cell containing a recombinant vector comprising introducing the recombinant vector according to claim 10 or 11 into a host cell.

13. A host cell produced by the method according to claim 12.

* * * * *